United States Patent [19]

Mendoza et al.

[11] Patent Number: 4,731,423

[45] Date of Patent: Mar. 15, 1988

[54] META-HALO-PHENOLIC ALKYLATION PRODUCTS AND EPOXY SYSTEMS

[75] Inventors: Abel Mendoza, Midland, Mich.; Chun S. Wang, Lake Jackson, Tex.; Eric E. Bancroft, Midland, Mich.; David B. Fritz, Lake Jackson, Tex.

[73] Assignee: The Dow Chemical Company, Midland, Mich.

[21] Appl. No.: 896,480

[22] Filed: Aug. 13, 1986

[51] Int. Cl.$^4$ .................... C08G 59/06; C08G 59/08; C07C 39/12

[52] U.S. Cl. ................ 525/480; 525/333.3; 525/359.6; 525/504; 525/509; 528/98; 528/102; 568/718; 568/720; 568/722; 549/559; 564/315

[58] Field of Search .............. 525/333.3, 359.6, 480, 525/504, 507; 568/637, 639, 718, 720, 722; 549/559; 528/98, 102; 564/315

[56] References Cited

U.S. PATENT DOCUMENTS

| | | | |
|---|---|---|---|
| 3,402,169 | 9/1968 | Jackson | 260/210 |
| 3,929,908 | 12/1975 | Orlando et al. | 260/620 |
| 3,956,403 | 5/1976 | Orlando et al. | 260/620 |
| 4,058,570 | 11/1977 | Kinson et al. | 260/620 |
| 4,266,054 | 5/1981 | Au | 544/215 |
| 4,377,712 | 3/1983 | Foster et al. | 568/637 X |
| 4,447,660 | 5/1984 | Jouannetaud et al. | 568/774 |
| 4,499,255 | 2/1985 | Wang et al. | 528/95 |
| 4,684,752 | 8/1987 | Mendoza | 568/779 |

FOREIGN PATENT DOCUMENTS 210615 10/1985 Japan.
1356508 6/1974 United Kingdom.

OTHER PUBLICATIONS

K. Auwers & H. Allendorf, *Ann.*, 302, 76–98 (1898).
Auwers et al., *Ann.*, 344, 95–141 (1906).
Auwers et al., *Ann.*, 356, 124–51 (1907).
Jacquesy et al., *J.C.S. Chem. Comm.*, 110–11 (1980).
K. Auwers & F. A. Trawn, *Ber.*, 32, 3309–17 (1899).
Wang, U.S. Ser. No. 851,996, filed 4/14/86.
So, U.S. Ser. No. 887,676, filed 7/17/86.

*Primary Examiner*—Earl Nielsen

[57] ABSTRACT

Titled materials and their preparation. The materials contain a moiety such as, for example, 4-oxy-3,5-dimethyl-2,6-dibromobenzyl which can impart a high degree of thermal and hydrolytic stability to the materials, for example, epoxy thermosets such as in electronic encapsulations. For example, when used in electronic encapsulation formulations, these materials can provide a substantial increase in electronic device reliability. Their preparation involves an alkylation of an aromatic ring, for example, such as a Friedel-Crafts alkylation with 4-bromomethyl-3,5-dibromo-2,6-dimethylphenol or with 4-hydroxymethyl-3,5-dibromo-2,6-dimethylphenol.

29 Claims, No Drawings

META-HALO-PHENOLIC ALKYLATION PRODUCTS AND EPOXY SYSTEMS

FIELD

The invention concerns halogenated coupled aromatic phenolic compounds, with a process to prepare them. These compounds are useful flame retardants, fungicides and monomers, especially for polymers such as engineering thermoplastics and epoxy thermosets. The invention integrally thus concerns such polymeric compositions.

BACKGROUND

Halogenated phenols are generally useful fungicides, monomers and flame retardants. Certain of the halogenated phenols and their derivatives, for example, brominated aromatic epoxy thermosets, are especially useful in the electronics industry.

However, bromination of most phenols and also certain novolacs is known to provide ring bromo-substitution at positions ortho or para to the phenolic hydroxyl group. See, for example, Jouannetaud et al., U.S. Pat. No. 4,447,660 (1984) and also Japan Kokai No. 60-210615 (85/210615).

Certain meta-halogenated phenols, for example, meta-brominated phenols, are generally known to be more thermally stable than their ortho-halogenated counterparts. See, for example, copending U.S. patent application Ser. No. 851,996, filed Apr. 14, 1986 (incorporated herein by reference). Unfortunately, only a few meta-brominated bisphenols have been described in the literature. K. Auwers & H. Allendorf, *Ann.*, 302, 76–98 (1898), reported the preparation of 2,2', 6,6'-tetrabromo-3,3',5,5'-tetramethyl-4,4'-dihydroxystilbene from 4-bromomethyl-3,5-dibromo-2,6-dimethylphenol. However, this solid is extremely insoluble, which limits its utility.

A more soluble solid is 2,2',6,6'-tetrabromo-3,3',5,5'-tetramethyl-4,4'-dihydroxydiphenylmethane, reported by Auwers et al., *Ann.*, 344, 95–141 (1906) and *Ann.*, 356, 124–51 (1907). It is reported to have been prepared by disproportionation in base of 4-aminomethyl-3,5-dibromo-2,6-dimethylphenol.

More recently, a number of meta-brominated biphenols have been prepared by the bromination of tetraalkyldiphenoquinones. See, for example, Orlando et al., U.S. Pat. Nos. 3,929,908 (1975) and 3,956,403 (1976) and Kinson et al., U.S. Pat. No. 4,058,570 (1977). Using this approach, bromination is the last step in the reaction sequence, and yields are only modest.

In the art of rendering flame-retardant otherwise more flammable materials, for example, thermoplastic polymeric substances such as polystyrenes, concerns include flame-retardant efficiency, formulation simplicity, ease of processability, retention of favorable structural properties and discoloration effects. Flame-retardant efficiency is typically related to the weight ratio of the flame-retardant rendering moiety such as, for example, weight of halogen of an organic halide, to the otherwise more flammable material. Flame-retardant efficiency can be decreased by ongoing processes such as, for example, oozing of the flame retardant. Typically, large amounts of the flame retardant may be thus added to increase the flame-retardant efficiency. In addition, typically large amounts of a flame-retardant synergist such as, for example, an antimony oxide, may be added to increase the flame-retardant efficiency of the flame retardant, for example, the organic halides. A typical formulation to obtain a UL 94 V-O rating may require about 12 weight percent bromine in an aromatic bromide and about 3.5 weight percent antimony oxide ($Sb_2O_3$). Moreover, the flame retardant itself may be difficultly processable into, or more importantly, adversely affect the structural properties of, the otherwise more flammable material, for example, the thermoplastics. See, for example, Great Britain Patent Specification No. 1,356,508 (1974). In addition, discoloration effects, for example, so-called "scorch" in a polyurethane, especially in flexible polyurethane foams, may be encountered in commercial production and are undesirable.

In the art of epoxy thermosets, for example, such as in electrical encapsulations and laminates, certain properties of the thermosets are desirable. For example, a higher glass transitoion temperature ($T_g$) coupled with higher hydrolytic stability such as measured by a low hydrolyzable halide content and with high flame-retardant efficiency is desirable in electrical encapsulations. However, presently available commercial electrical encapsulation systems derived from cresol epoxy novolacs and bis(4-(2,3-epoxypropoxy)-3,5-dibromophenyl)isopropylidene with bromo moieties ortho to the 4-oxy moiety, although of high flame-retardant efficiency (UL 94 V-O rating) and good thermal stability ($T_g$ 155° C., by T.M.A., Thermo Mechanical Analyzer), are hydrolytically unstable (hydrolyzable bromide 180 parts per million (ppm) as measured by total hydrolyzable halide method herein). For example, this hydrolytic instability, even when coupled with the moderately high thermal stability, is problematical because when coupled with moisture penetration, can result in internal corrosion of the encapsulated device, thereby reducing or destroying the effectiveness especially of microelectric circuitry. The moderately high thermal stability itself is also a property needing improvement. A major reason for this is the miniaturization in the art of so-called "microchip" technology. As the scale of these microchips becomes increasingly smaller, the localized heat problems become increasingly greater, and thus, the present encapsulation formulation properties may not be as suitable as desired. In the art of electrical laminates, many of these same considerations apply.

SUMMARY

The invention, in one aspect, is novel meta-halo-phenylic-coupled aromatics. Another aspect is a process for preparing a meta-halo-phenylic-coupled aromatic comprising contacting a para-(hm)methyl-meta-halophenylic with another aromatic compound under conditions whereby the meta-halo-phenylic-coupled aromatic is prepared. The meta-halo-phenylic-coupled aromatics range in form from monomers useful for example, for engineering thermoplastics and epoxy thermosets, for example, in electronics, to polymers which are, for example, the engineering thermoplastics and epoxy thermosets therefrom or which are polymers modified with the meta-halo-phenylic-coupled aromatics.

ILLUSTRATIVE EMBODIMENTS

In general, the meta-halo-phenylic-coupled aromatic is a material containing at least one "azachalcohalomesitylic" moiety. The azachalcohalomesitylic moiety is a moiety such as one having at least one halogen (halo)

moiety in a position meta to nitrogen or chalcogen singly-bonded onto an aromatic nucleus of a six-membered carbocyclic aromatic ring. Said aromatic nucleus has a methylene moiety, which is in a position para to said nitrogen or chalcogen and which is also bonded to the carbon of another aromatic ring. Generally also, said nitrogen or chalcogen is a part of a moiety such as an amino (—$NH_2$), substituted amino (—NHR; —$NR_2$), amido (—NHC(O)R'), bisamido (—$N(C(O)R')_2$) (imide) moiety, or urethane (—NHC(O)OR'); a hydroxy (—OH) moiety or an organooxy (—OR), for example, such as an alkoxy, especially $C_{1-4}$ alkoxy, for example, methoxy (—$OCH_3$) moiety, or, methyleneoxy (—$OCH_2$—) moiety substituted, or example, with additional ether linkage methylene chains, methyl capped, or with hydroxy moiety or an ester moiety (—OC(O)R') such as, for example, acetoxy (—$OC(O)CH_3$); or a mercapto (—SH) moiety or organothioxy (—SR) moiety analogous to the organo-oxy.

Preferably, the meta-halo-phenylic-coupled aromatic contains at least about 0.3 percent by weight from the azachalcohalomesitylic moiety present, more preferably at least about 2 percent by weight and most preferably at least about 7 percent by weight. It is especially preferred that at least about 10 percent by weight of the azachalcohalomesitylic moiety is present in the meta-halo-phenylic-coupled aromatic and more especially at least about 20 percent by weight.

The R group(s) in the foregoing illustrations is (are separately at each occurrence) $C_{1-r}$ organic. (organic group with from one to about r carbons). Preferably, the organic (R) group is hydrocarbyl. The r is an integer, preferably maximally about 12 in the case of a generally monomeric meta-halo-phenylic-coupled aromatic, and otherwise up to the number of carbons found in a particular generally polymeric material. The R' group(s) is (are separately at each occurrence) $C_{1-(r-1)}$ organic (organic group with from one to about the difference of the value of r minus one). Thus, for example, with the organic group alkyl and the value of r equal to 4, the $C_{1-r}$ organic (R) group is methyl, ethyl, n-propyl, isopropyl, n-butyl, isobutyl, sec-butyl or t-butyl, and the $C_{1-(r-1)}$ (R') group is methyl, ethyl, n-propyl or isopropyl such as, for example, in the acetoxy moiety or corresponding propionoxy or butyryloxy moiety. The R and R' (generally monomeric) groups are preferably $C_{1-8}$ hydrocarbyl such as, for example, in a phenyl, tolulyl, xylenyl or ethylphenyl aromatic moiety or in aliphatic moieties, especially the alkyl moieties.

Examples of carbocyclic moieties within the ambit of the azachalcohalomesitylic moiety are moieties such as, for example, azachalcohalomesitylic naphthics

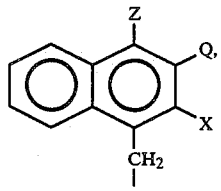

azachalcohalomesitylic cycloaliphatic phenics (I)

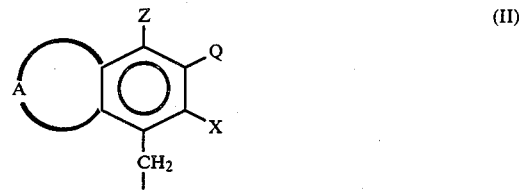

and azachalcohalomesitylic phenics

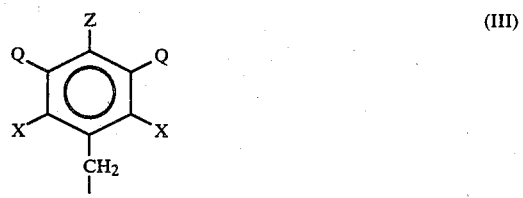

wherein each of the moieties of the formulae (I), (II) and (III), as appropriate, A is an aliphatic ring system bonded to the aromatic (phenic) ring;

Q is separately at each occurrence methyl, or other alkyl with primary (1°) or secondary (2°) saturated carbon moiety bonded directly to the arenic ring, or generally inertly-substituted alkyl, each preferably maximally of about 12 carbons ($C_{1-12}$), or hydro (—H), more preferably the alkyl and most preferably methyl;

X is (separately at each occurrence) halo, which includes fluoro (F), chloro (Cl), bromo (Br) and iodo (I), preferably F, Cl or Br, more preferably Cl or Br and most preferably Br; and Z is said singly bonded nitrogen- or chalcogen-containing moiety, preferably the corresponding oxygen-containing moiety (hence, "oxyhalomesitylic") such as, for example, hydroxy.

By arenic is meant an aromatic ring or ring system which can include those such as the naphthics and the phenics.

Examples of heterocyclic fused ring moieties within the ambit of the azachalcohalomesitylic moiety are moieties such as, for example, 5- and 8-azachalcohalomesitylic quinolines (a) and (b) isoquinolines (c), respectively

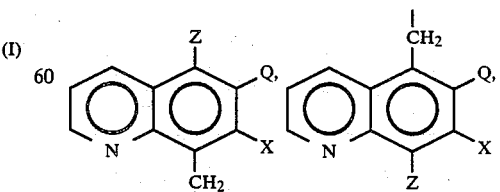

(IV(a))    (IV(b))

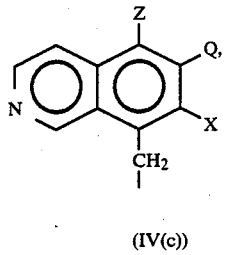

(IV(c))

wherein Q, X and Z are as in the azachalcohalomesitylic moieties of the formulae (I), (II) and (III).

Not as preferred, but also within the ambit of the azachalcohalomesitylic moiety are moieties such as substituted fused or cycloaliphatic ring variants of the azachalcohalomesitylic moieties of the formulae (I), (II), (IVa) and (IVb) such as substituted with other fused or cycloaliphatic ring systems, also hydrocarbyl groups, for example, methyl and ethyl. However, such are preferably methyl-substituted such as at the ortho position in relation to the Z moiety of the azachalcohalomesitylic moieties of the formulae (I), (IVa) and (IVb).

Preferred are the carbocyclic azachalcohalomesitylic moieties. Preferred of the carbocyclic azachalcohalomesitylic moieties are the azachalcohalomesitylic phenics of the formula (III), especially the oxyhalomesitylic.

Preferably, halo moieties are at both meta positions to the nitrogen or chalcogen singly bonded to the aromatic nucleus. Preferably, the meta halo moieties are selected from the group consisting of fluoro, chloro and bromo, more preferably, chloro and bromo, and most preferably the meta halo moieties are each bromo.

More preferably, the oxyhalomesitylic moiety is represented by the formula:

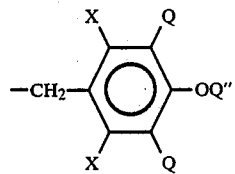

(IIIa)

wherein
Q is separately at each occurrence methyl or other alkyl (with 1° or 2° saturated carbon bonded directly to the phenol ring) or generally inertly-substituted alkyl, each preferably $C_{1-12}$ alkyl or substituted alkyl, or hydrogen, more preferably the alkyl and most preferably methyl;
Q" is hydrogen or the organo-oxy, preferably hydrogen or such as beta, gamma-epoxypropylene or beta-halo, gamma-oxy-propane; and
X is separately at each occurrence one of the meta-halo moieties.

Thus, the most especially preferred of the oxyhalomesitylic moieties are 4-hydroxy-3,5-dimethyl-2,6-dibromobenzyl or such as 4-(2,3-epoxypropoxy)-3,5-dimethyl-2,6-dibromobenzyl, or 4-(1-oxy-2-hydroxy-3-halopropane)-3,5-dimethyl-2,6-dibromobenzyl.

The azachalcohalomesitylic moiety can be bonded (coupled) to a ring carbon in the other mentioned aromatic ring which can be heterocyclic such as, for example, 2-pyridinol, or carbocyclic such as, for example, in benzene ring, naphthalene ring, anthracene ring or cyclopentadiene ring systems, and so forth and the like.

Thus, the azachalcohalomesitylic moiety can be generally coupled to an aromatic carbon of all aromatic-containing compounds for monomers, and to polymers such as, for example, polystyrenes, or modified polystyrenes such as, for example, polymer blends with polystyrene or chloromethylated polystyrenes, copolymers containing polystyrenes such as, for example, ABS resins, styrene-divinylbenzene copolymers and styrene-acrylonitrile copolymers, polycarbonates and copolymers thereof such as polyester carbonates and polyether carbonates and polymer blends therewith, polyphenylene sulfides and copolymers thereof and polymer blends therewith, aromatic polyesters and copolymers thereof and polymer blends therewith, polyether sulfones and copolymers thereof and polymer blends therewith, polyphenylene oxides and copolymers thereof and polymer blends therewith and polyaryl ether ketones and copolymers thereof and polymer blends therewith and so forth. Preferably, the azachalcohalomesitylic moiety is attached to an aromatic ring system which itself contains at least one aromatic hydroxy moiety such as, for example, in phenols (V), aromatic diols (VI), diphenolics (VII), trisphenols (VIII), polyvinyl phenols (IX), novolac resins (X), polycyclopentadiene polyphenols (XI), each of the following formulae

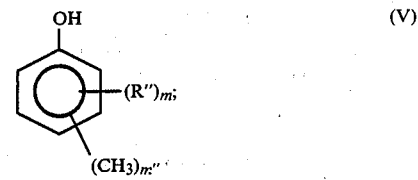

(V)

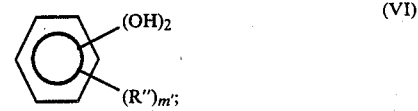

(VI)

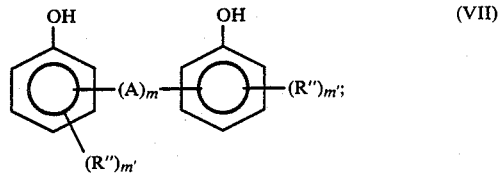

(VII)

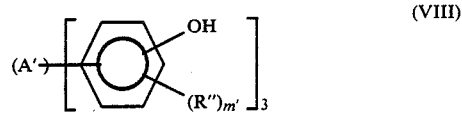

(VIII)

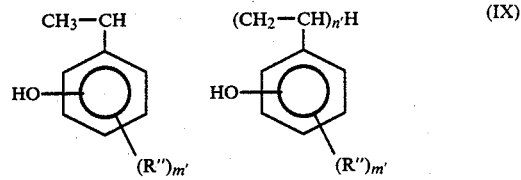

(IX)

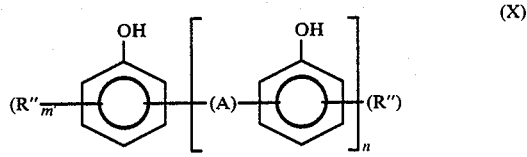

(X)

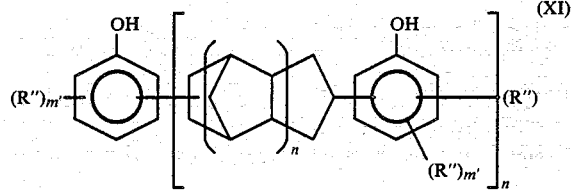

wherein each of the substances of the formulae (V through XI, inclusive), as appropriate, A is a divalent organic group (or a direct bond between the rings such as in biphenyl systems), more preferably a divalent hydrocarbyl group, for example, methylene (—CH$_2$—);

A' is a trivalent organic group, more preferably a trivalent hydrocarbyl group, for example, methylyne (—CH—);

R" is hydro or an alkyl or aryl organic group, more preferably the alkyl group, halo or organo-oxy for example, methyl;

m is separately at each occurrence an integer from zero to 4, more preferably zero to 2;

m' is separately at each occurrence an integer from zero to 2, more preferably one;

m" is zero or one (cresols);

n is separately at each occurrence an integer from one to about 10, more preferably one to 6; and n' is an integer from one to about 100, more preferably to about 50 and most preferably is about 25.

Also, the azachalcohalomesitylic moiety is preferably attached to the arene ring system of the appropriately unsubstituted arene rings of compounds disclosed in copending U.S. patent application Ser. No. 887,676, filed July 17, 1986 now abandoned (incorporated herein by reference), for example, such as the multi((hydroxy/mercapto or other hydrochalco)benzoyl)benzenes or substituted variants thereof. More preferably, the therein disclosed compound is 1,4-bis(4-hydroxybenzoyl)benzene. Epoxidation can follow, if desired.

The so-called alkylated products thus can be illustrated by the following exemplary formulae

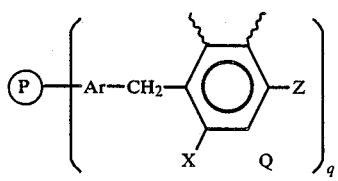

especially such as, for example,

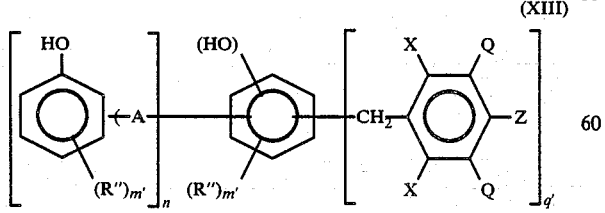

wherein
Q, R", X and Z are as defined for the azachalcohalomesitylic moieties of the formulae (I) through (III);

Ar is an aromatic ring;

(P) is a polymeric substance to which the Ar, aromatic ring, is bonded;

m' is separately at each occurrence an integer from zero to 2, more preferably one;

q is an integer from one to a number limited by the length of any polymer chain as represented; and q' is an integer from one to 4, especially one to 3, representing the number of azachalcohalomesitylic moieties bonded to each other aromatic ring (Ar or

for example.

The para-(hm)methyl-meta-halophenylic means para-(hetero moiety)methyl-meta-halophenylic. Thus, the parenthetical recitation "hm" is a "hetero moiety" substituted onto the para-methyl group. For example, the hetero moiety can be HALO, that is, a halo moiety selected from bromo (Br) and chloro (Cl), preferably bromo, and the resulting para-(hm)methyl group would thus be para-HALOmethyl (4-HALOmethyl). Or, the hetero moiety can be hydroxy, and the resulting para-(hm)methyl group would thus be para-hydroxymethyl. Other of such suitable hetero moieties are those such as, for example, methoxy, ethoxy and acetoxy. In general, the hetero moiety is one which can form a by-product such as a hydro-adduct, (H(hm)) with a moiety such as the hydro moiety of the other aromatic ring in the preparation of the meta-halo-phenylic-coupled aromatic. The para-(hm)methyl-meta-halophenylic is a suitable source of the azachalcohalomesitylic moiety.

The para-(hm)methyl-meta-halophenylic also contains at least one moiety such as a halo moiety in a position meta to nitrogen or chalcogen singly-bonded onto an aromatic nucleus such as a six-membered aromatic ring. Preferably, said nitrogen or chalcogen, and preferably oxygen, is a part of a moiety such as a, for example, an amino, mercapto or hydroxy moiety and more preferably the hydroxy moiety, although, for example, said oxygen can be part of an organo-oxy moiety, especially such as, alkoxy, for example, methoxy or inertly-substituted variant thereof, wherein inertly refers to a substituted moiety which does not generally interfere with the process for preparing the meta-halo-phenylic-coupled aromatic. Similarly, said nitrogen or other chalcogen can be part of a moiety such as secondary amino or, for example, organo-thiol (R—SH).

Preferably, halo moieties of the para-(hm)methyl-meta-halophenylic are at both meta positions of a six-membered aromatic carbon ring. Preferably, the meta-halo moieties are selected from the group consisting of fluoro, chloro and bromo, more preferably, chloro and bromo, and most preferably, the meta-halo moieties are each bromo.

More preferably, the para-(hm)methyl-meta-halophenylic is a para-(hm)methyl-dimeta-halophenolic such as represented by the formula

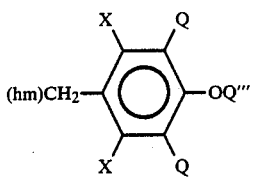

(XIV)

wherein
- (hm) is the hetero moiety, preferably hydroxy, the HALO or methoxy, most preferably hydroxy or bromo;
- Q is separately at each occurrence alkyl (with at most secondary (2°) carbon bonded directly to the phenol ring) or generally inertly-substituted alkyl, each preferably $C_{1-12}$, or hydro, more preferably the alkyl and most preferably methyl;
- Q''' is hydro or inert organo-oxy (that is, organo-oxy moiety which does not generally interfere with the process of the invention) such as acetyl, or such as alkyl, preferably such as, for example, methyl, and most preferably hydro; and
- X is separately at each occurrence one of the meta-halo moieties.

Thus, the most especially preferred of the para-(hm)methyl-dimeta-halophenolics include, for example, 4-bromomethyl-3,5-dibromo-2,6-dimethylphenol and 4-hydroxymethyl-3,5-dibromo-2,6-dimethylphenol.

The para-(hm)methyl-meta-halophenylics can be prepared by known procedures or by a procedure disclosed or referenced herein. For example, ortho alkylation of phenols is well-known in the art. The ortho alkylation of 1-naphthol or tetrahydro-1-naphthol or the quinolines (commercial materials available from Aldrich Chemical Company) affords a 2-alkyl phenol or appropriately corresponding alkyl quinoline; 2-methyl-1-naphthol is readily available. Bromination of these phenols or alkylated quinolines in super-acids using the general procedure of Jacquesy et al., *J. C. Soc. Chem. Comm.*, 110–11 (1980), affords the meta-brominated phenols or quinolines. Further functionalization of these phenols or quinolines to prepare hydroxymethyl or chloromethyl derivatives uses well established procedures.

Also, para-HALOmethyl-dimeta-halo-diortho-substituted phenols (that is, 4-HALOmethyl-3,5-dihalo-2,6-disubstituted phenols) are preferably prepared by the process of copending U.S. patent application Ser. No. 858,473, filed Apr. 30, 1986, now U.S. Pat. No. 4,684,752, issued Aug. 4, 1987 (incorporated herein by reference). The para-hydroxymethyl-dimeta-halo-2,6-disubstituted phenols can then be prepared by reacting the para-HALOmethyl-dimeta-halo-diortho-substituted phenols with water in acetone such as by the general procedure of K. Auwers & H. Allendorff, *Ann.*, 302, 76–98 (1898) or by reacting such as, for example, 3,5-dibromo-2,6-dimethylphenol with formaldehyde by the general procedure of K. Auwers & F. A. Trawn, *Ber.*, 32, 3309–17 (1899).

Corresponding ortho-hydro phenolics can be prepared by isomerizing ortho-bromophenols into corresponding meta-brominated derivatives in the presence of a liquid superacid as generally described by Jouannetaud et al., U.S. Pat. No. 4,447,660 (1984) (incorporated herein by reference). Corresponding organo-oxy (including, of course, organo-oxy moieties of the "hetero moiety") can be prepared from the para-hydroxymethyl-meta-halophenolics by standard Williamson ether synthesis or by the general procedure of K. Auwers & H. Allendorff, *Ann.*, 302, 76–98 (1898).

The other aromatic can be virtually any aromatic compound to which the para-(hm)methyl-meta-halophenylic is contacted with to prepare the meta-halo-phenylic-coupled aromatic such as would contain the other mentioned aromatic rings to which the aza-chalcohalomesitylic moiety is coupled. Preferred are the hydroxy aromatics such as of the formulae (V) through (XI), especially alkyl phenols and cresol formaldehyde novolacs.

The meta-halo-phenylic-coupled aromatics are prepared by contacting the para-(hm)methyl-meta-halophenylic with the other aromatic compound. Conditions are those sufficient to carry out the coupling reaction.

The conditions of the coupling can appropriately be those generally encountered in known alkylation couplings. For example, conditions can be those generally encountered in Friedel-Crafts alkylations. Friedel-Crafts alkylation conditions can include employment of a Lewis acid or Bronsted acid catalyst such as, for example, aluminum tribromide, aluminum trichloride or ferric chloride, or a protic acid, an inert organic diluent such as a haloalkane, for example, dichloromethane, temperatures from about 20° C. to about 150° C., typically ambient pressures and times from about 10 minutes (600 seconds) to about 14 hours (50,400 seconds) depending on the conditions, for example, by an increase in temperature or by an increase in the level of catalyst.

In general, a by-product such as the corresponding H(hm) compound is prepared from the coupling. For example, with 4-hydroxymethyl-3,5-dibromo-2,6-dimethylphenol employed as the para-(hm)methyl-meta-halophenylic, a by-product of water is thus typically produced, and the corresponding halide from the para-HALOmethyl group appears as a by-product of the Friedel-Crafts alkylation, most typically as HCl or HBr. Other H(hm) compounds such as, for example, methanol or acetic acid, as is appropriate for each hetero moiety, methoxy or acetoxy, respectively, are also typically produced as a useful by-product.

Preferably and even more unexpectedly, the para-(hm)methyl-meta-halophenylics, especially the para-(hm)methyl-dimeta-halophenolics, do not generally require the addition of catalysts, for example, Lewis acid or Bronsted acid catalysts. The alkylation may thus be acatalytic, self-catalytic or catalyzed by minute amounts of impurities normally present in the reaction mixture or on the reaction vessel.

More preferred temperature ranges include those such as from about 20° C. to about 100° C. with the employment of additional Bronsted or Lewis acid catalyst. Temperatures from about 80° C. to about 220° C. are generally preferred when the alkylation is carried out without added catalyst. Typically, temperatures such as from about 80° C. to about 150° C. are more preferred without added catalyst in the case of alkylation of the lower molecular weight other aromatics, for example, pyridinols, phenolics and novolacs, and typically even higher temperatures are preferred when thus alkylating the higher molecular weight polymeric materials, for example, polystyrenes.

An inert diluent is preferably present. Preferably, the inert diluent is one which can form a low-boiling azeotrope with the by-product such as the H(hm) by-products. For example, benzene, toluene or methyl isobutylketone (MIBK), with an aqueous by-product.

Etherification of meta-halo-phenylic-coupled aromatics, for example, the hydroxy-containing ones (that is, meta-halo-phenylic-coupled aromatics), for example, 4-hydroxy-3,5-dimethyl-2,6-dibromobenzyl (oxyhalomesitylic) moiety containing coupled benzenes and phenols up through the novolacs can be next carried out, if desired, to prepare hydroxy-containing organo-oxy moieties by reacting an oxirane therewith by generally known procedures such as, for example, that of Jackson, U.S. Pat. No. 3,402,169 (1968) (incorporated herein by reference). Preferably, the etherification is carried out with an epihalohydrin such as, for example, epichlorohydrin or epibromohydrin. The amino- and mercapto-containing meta-halo-phenylic-coupled aromatics react similarly to the hydroxy-containing ones, generally preparing amino- or mercapto-containing epoxy resins.

When the oxirane employed to carry out the etherification is such as the epihalohydrins, a vicinal halohydrin organo-oxy moiety is preferably obtained, wherein halo and hydroxy moieties are on adjacent terminally ended carbons such as, for example, in a 3-chloro-2-hydroxypropoxy moiety. Preferably, the vicinal halohydrin organo-oxy moiety-containing meta-halo-phenylic-coupled aromatic is epoxidized to obtain a meta-halo-phenylicoxyepoxy-coupled aromatic such as containing a terminally ended epoxy group, for example 2,3-epoxypropoxy.

The epoxidation can be carried out with epoxidizing agents such as an aqueous alkali metal hydroxide in a biphasic reaction system, such as by the general procedure of Wang et al., U.S. Pat. No. 4,499,255 (1985) or by the general procedure of Au, U.S. Pat. No. 4,266,054 (1981) (each incorporated herein by reference). Preferably, the epoxidation is carried out with aqueous sodium hydroxide employing as the organic phase diluent an inert organic diluent such as a saturated ether or ether-alcohol. The ether-alcohol is preferably one such as, for example, 1-methoxy-2-hydroxypropane.

The meta-halo-phenylicoxyepoxy-coupled aromatics can be cured into meta-halo-phenylic-coupled aromatic epoxy thermosets by employment or a curing agent, for example, a hydroxy-containing organic compound. Preferably, the curing agent contains one or more of compounds such as primary aliphatic and aromatic amines, guanidines, biguanides, polycarboxylic acids and anhydrides thereof, amides, sulfones, sulfonamides and polyhydric phenols, with preferred species also including bis(4-aminophenyl)sulfone, aminophenyl sulfonamide, dicyandiamide, phenylenediamide and phthalic anhydride. The phenol formaldehyde novolacs, including meta-halo-pheno-coupled aromatic novolacs, are preferred curing agents in formulations such as for electronic encapsulation. These novolacs herein preferably contain from about 1 to 20 percent by weight bromine, more preferably from about 5 to about 15 percent by weight bromine, especially as from meta-bromo moieties, or at least about half that from the lighter molecular weight halogens. The curing agent, thus more preferably contains a phenol formaldehyde novolac or a hydroxy-containing compounds such as, for example, 4-hydroxymethyl-3,5-dibromo-2,6-dimethylphenol and/or meta-halo-phenylic-coupled aromatic novolacs. Alternatively, the meta-halophenoxy-coupled aromatic can be used as the curing agent to cure a thermosettable epoxy such as a cresol epoxy novolac to afford a cured epoxy thermoset composition containing the azachalcohalomesitylic moiety.

In general, the meta-halo-phenylic-coupled aromatics typically possess unusually high hydrolytic and thermal stability. Thus, for example, the meta-halo-phenylic-coupled aromatic cured epoxy thermosets can be generally employed as part of an electronic encapsulation material which preferably has flame-retardant capability and very low hydrolyzable halide content upon heat or moisture exposure. For example, when used in electronic encapsulation formulations, these materials can provide a substantial increase in electronic device reliability. Preferably, the electronic encapsulation material is prepared with the meta-bromo-phenylic-coupled aromatic cured epoxy systems. Preferred electronic encapsulation formulations include those employing the following meta-bromo-phenylic-coupled aromatics:

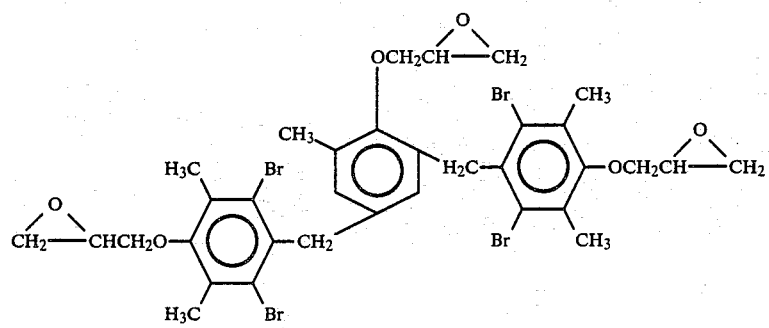

(XV)

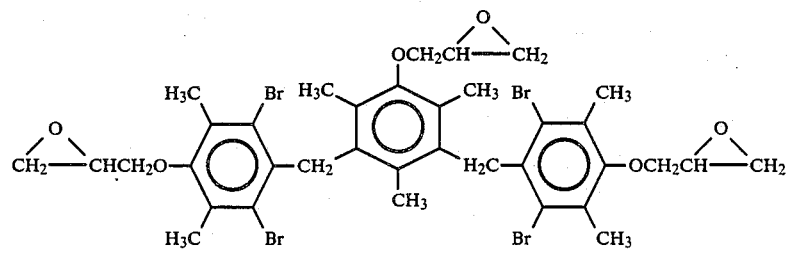

(XVI)

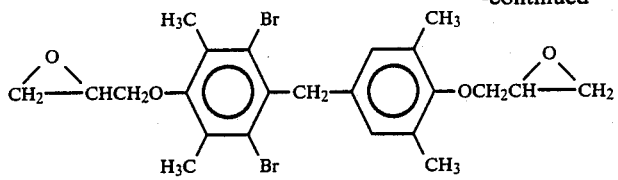
(XVII)

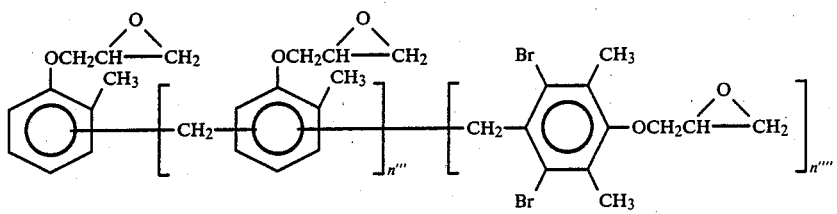
(XVIII)

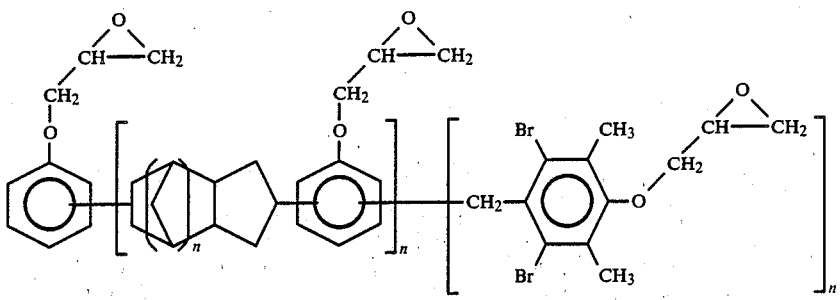
(XIX)

wherein n is separately at each occurrence an integer from one to about 10, more preferably one to 6; n''' is generally from zero to 100, preferably from about 2 to about 10; and n'''' is the same as n''' but preferably is less, more preferably from one to about 5.

Of these compounds of the formulae (XV through XIX), the compounds of the formulae (XVII through XIX) are more preferred, and even more preferred are the compounds of the formulae (XVIII and XIX).

Preferably, the amounts of the hydroxy- (or other such active hydrogen) containing compounds (e.g., novolac; thiol; amino) as "curing agents" are employed with the epoxy compound in a ratio of about the stoichiometric ratio. The stoichiometric ratio is one molar equivalent of such active hydrogen-containing moieties in the compound (e.g., one molar equivalent of —OH or —SH or one-half equivalent of —NH$_2$) with one molar equivalent of the epoxy moieties, generally as a glycidyl ether moiety, in the other compound. However, see, the incorporated U.S. patent application Ser. No. 851,996, filed Apr. 14, 1986. Preferably herein, final bromine content of the encapsulation formulation is from about 0.5 to 3 percent by weight, more preferably from about 1 to 2 percent by weight.

SPECIFIC EMBODIMENTS

The following examples further illustrate the invention. Parts and percentages are by weight unless otherwise noted.

EXAMPLES 1-14

Alkylations with 4-bromomethyl-3,5-dibromo-2,6-dimethyl phenol (tribromomesitol):

EXAMPLE 1

Monoalkylation of 2,6-Dimethylphenol

A 372-9-g (1.0-mole) portion of 4-bromomethyl-3,5-dibromo-2,6-dimethylphenol (tribromomesitol) and 122.2 g (1.0 mole) of 2,6-dimethylphenol are dissolved in 3.0 liters of methylene chloride at 20° C. and 0.15 g of ferric chloride is added. The solution is gently heated to 40° C. over a period of one hour. Subsequent to heating for a few minutes, a precipitate begins to form. HBr gas is evolved during the heating period. At the moment the temperature reaches 40° C., the slurry is refluxed for 0.5 hour, is cooled to 25° C., and the insoluble solid is filtered and is dried. This affords 372.7 g of crude, white solid which is analyzed as 99+ percent purity dibromotetramethylbisphenol F by gas chromatography (90 percent yield) which has the following nuclear magnetic resonance spectrum: (acetone d$_6$), delta: 2.20 (s, 6H), 2.40 (s, 6H0, 4.30 (s, 2H), 6.60 (s, 2H). This is consistent with the structure of the product. Recrystallization from 2.0 liters of toluene affords 335.0 g of solid of 99.9+ percent purity by gas chromatography. This latter solid melts at 210° C.-211° C. and is identified as

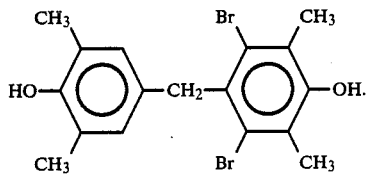

EXAMPLE 2

Monoalkylation of ortho-Cresol

A 175.0-g (0.47-mole) portion of tribromomesitol and 150 g (1.39 moles) of ortho-cresol are dissolved in 1.5 liters of carbon tetrachloride at 20° C., and 0.20 g (0.0012 mole) of ferric chloride is added. The solution is heated to 45° C. over a period of one hour. During this time a precipitate appears. The slurry is heated to 70° C. to complete the evolution of HBr gas, and is held there for 0.5 hour. Cooling to 25° C. and filtering of the insoluble solid affords 139.0 g (74 percent yield) of dibromotrimethylbisphenol F, identified by liquid chromatography as 99+ percent purity para-alkylated material. The solid has the following H nuclear magnetic resonance spectrum: (acetone d$_6$), delta: 2.20 (s, 3H), 2.40 (s, 6H), 4.30 (s, 2H), 6.60 (s, 2H), 6.80 (s, 1H), and melts at 197° C.-199° C. The insoluble solid is identified as

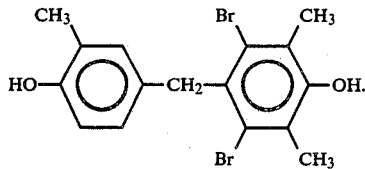

EXAMPLE 3

Monoalkylation of Phenol

A 372.9-g (1.0-mole) portion of tribromomesitol and 282.0 g (3.0 moles) of phenol are dissolved in 2.5 liters of carbon tetrachloride at 20° C., and 0.3 g (0.0018 mole) of ferric chloride is added. The solution is heated to 45° C. over a period of one hour. A solid precipitates during this period. The slurry is heated to reflux temperature, and 1.0 liter of solvent is removed. Cooling to 25° C. affords 203.2 g of a slightly yellow solid which, when analyzed by liquid chromatography, has the following composition: 2 percent tribromomesitol, 4 percent phenol, 90 percent monoalkylated phenol as a mixture of isomers, and 4 percent dialkylated phenol. Further purification of the crude solid from 1.0 liter of hot carbon tetrachloride, by refluxing for 0.5 hour affords 180.0 g of a product which contains 92 percent of the para-alkylated phenol.

The solid has the following H nuclear magnetic resonance spectrum: (acetone d$_6$), delta: 2.40 (s, 6H), 4.30 (s, 2H), 6.6-7.2 (m, 4H), and melts at 168° C.-175° C. The latter solid is identified as

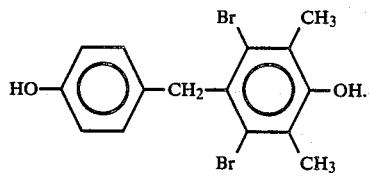

EXAMPLE 4

Dialkylation of ortho-Cresol

A 313.0-g (0.84-mole) portion of tribromomesitol and 43.2 g (0.40 mole) of o-cresol are dissolved in 3.5 liters of methylene chloride at 20° C., and 0.3 g (0.0018 mole) of ferric chloride is added. The solution is heated to 40° C. over a period of one hour, and the slurry which is obtained is refluxed for one more hour. Removing 1.0 liter of solvent and cooling to 25° C. affords 255.0 g of solid, which analyzes by liquid chromatography as 98 percent dialkylated product, with 1 percent monoalkylated and 1 percent trialkylated o-cresol.

The solid has the following H nuclear magnetic resonance spectrum: (acetone d$_6$), delta: 2.20 (s, 3H), 2.30 (s, 6H), 2.40 (s, 6H), 4.20 (s, 2H), 4.40 (s, 2H), 5.80 (s, 1H), 6.80 (s, 1H), and melts at 224° C.-226° C. The solid is identified as

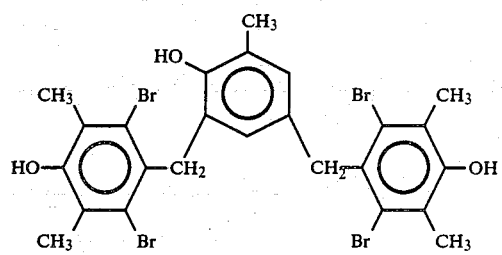

EXAMPLE 5

Dialkylation of 2,4,6-Trimethylphenol

A 392.0-g (1.03-mole) portion of tribromomesitol and 68.1 g (0.50 mole) of 2,4,6-trimethylphenol are dissolved in 3.0 liters of carbon tetrachloride at 20° C., and 1.0 g (0.006 mole) of ferric chloride is added. The solution is heated to reflux and is held there for 7.0 hours. Some solid precipitates during this time. Removing 1.0 liter of solvent and cooling to 25° C. affords 286.3 g of solid (76 percent yield) of 96 percent purity by liquid chromatography, containing 4 percent monoalkylated product. The solid has the following H nuclear magnetic resonance spectrum: (acetone d$_6$), delta: 1.80 (s, 3H), 2.10 (s, 6H), 2.30 (s, 12H), 4.40 (s, 4H). The solid is purified by slurrying in hot methylene chloride, cooling to 25° C., and filtering to afford 99 percent purity dialkylated mesitol, which melts at 164° C.-166° C. The latter solid is identified as

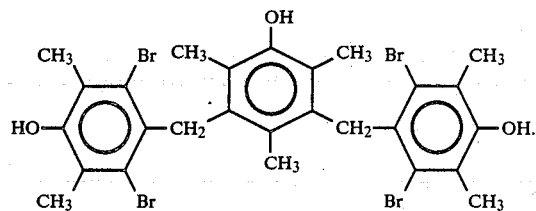

EXAMPLE 6

Dialkylation of Tetramethylbiphenol

A 7.50-g (0.020-mole) portion of tribromomesitol and 2.40 g (0.010 mole) of tetramethylbiphenol are suspended in 100 ml of carbon tetrachloride, and 0.10 g (0.0006 mole) of ferric chloride is added. The mixture is heated to reflux and held there for 5.0 hours. Cooling of the slurry and filtration of the insoluble solid affords 6.04 g of product. Analysis by liquid chromatography indicates 84 percent dialkylated product and 16 percent monoalkylated material. The solid melts at 221° C.-226° C., and has the following H nuclear magnetic resonance spectrum: (acetone d$_6$), delta: 1.90 (s, 6H), 2.10 (s, 6H), 2.20 (s, 12H), 4.10 (s, 4H), 4.30 (small s), 6.20 (s, 2H). The solid is identified as

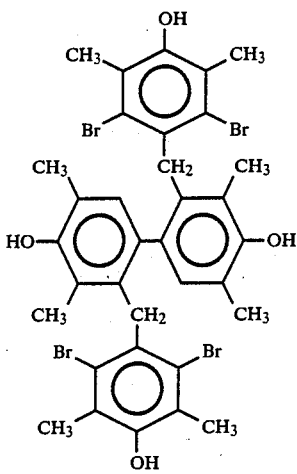

EXAMPLE 7

Alkylation of Dicyclopentadienebisphenol Novolac

A 3.7-g (0.01-mole) portion of tribromomesitol and 3.5 g of dicyclopentadienebisphenol novolac of 2.2 hydroxy functionality is dissolved in 100 ml of methylene chloride, and 0.008 g (0.05 mmole) of ferric chloride is added. The solution is refluxed for 8.0 hours, is cooled, and the solent is removed in a rotary evaporator. This affords 6.5 g of product. Complete reaction of the tribromomesitol to alkylation products is shown when it is analyzed by nuclear magnetic resonance spectroscopy: a singlet of 4.3 delta for the methylene group of the alkylated products. The methylene singlet for tribromomesitol appears at 4.90 delta.

EXAMPLE 8

Monoalkylation of Chlorobenzene

A 7.46-g (0.02-mole) portion of tribromomesitol is suspended in 100 ml of chlorobenzene (0.98 mole), and 0.02 g (0.00012 mole) of ferric chloride is added. The mixture is heated to reflux and is held there for 4 hours. The solution is cooled, and the solvent is removed in a rotary evaporator. A brown oil is obtained which is recrystallized from hexane, which affords 4.7 g of solid which is identified by H nuclear magnetic resonance and mass spectrometry as the monoalkylated product. H nuclear magnetic resonance spectrum: (CDCl$_3$), delta: 2.34 (s, 6H), 4.44 (s, 2H), 7.12 (m, 4H). The oil is identified as a mixture of isomers:

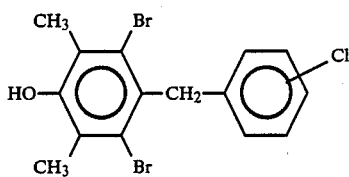

EXAMPLE 9

Monoalkylation of Benzene

A 9.30-g (0.025-mole) portion of tribromomesitol is added to 100 ml of benzene (1.12 moles), and 0.02 g (0.0012 mole) of ferric chloride is added. The mixture is heated to reflux and is held there for 1.5 hours. Cooling of the solution, filtration of insoluble solid and removing the solvent by a rotary evaporator affords 8.10 g of crude product which is identified by its H nuclear magnetic resonance spectrum as the monoalkylated product. H nuclear magnetic resonance spectrum: (CDCl$_3$), delta: 2.33 (s, 6H), 4.48 (s, 2H), 7.16 (m, 5H). The product is identified as

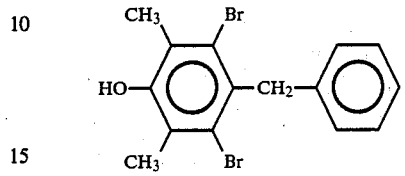

EXAMPLE 10

Dialkylation of Benzene

A 112.0-g (0.30-mole) portion of tribromomesitol and 13.0 ml (0.146 mole) of benzene are dissolved in 1.2 liters of methylene chloride, and 0.10 g (0.0006 mole) of ferric chloride is added. The solution is heated to reflux and is held there for 2.0 hours. A solid precipitates during the refluxing period. The slurry is cooled to 25° C., and the insoluble solid is filtered. This affords 85.6 g of white solid. The crude solid is purified by slurrying in 250 ml of acetone and filtering, which affords 81.7 g (96 percent yield) of solid which is identified as the dialkylated benzene by liquid chromatography. The purified solid has the following H nuclear magnetic resonance spectrum: (DMSO d$_6$+CCl$_4$, 1:1), delta: 2.31 (s, 12H), 4.34 (s, 4H), 6.92 (s, 4H). The solid does not melt at temperatures at or below 300° C. The purified solid is identified as

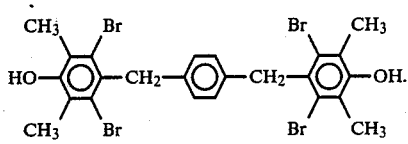

EXAMPLE 11

Dialkylation of meta-Xylene

A 198.0-g (0.53-mole) portion of tribromomesitol is dissolved in 2.0 liters of methylene chloride at 20° C., and 0.20 g (0.0012 mole) of ferric chloride is added. The solution is heated to 35° C., and 30.6 ml (0.25 mole) of meta-xylene is added over a period of 10 minutes. HBr gas is evolved during the addition, and a precipitate appears. The slurry is refluxed for 1.5 hours, 1.0 liter of solvent is removed, and the insoluble solid is filtered after cooling to 25° C. This affords 136.0 g of dialkylated product (79 percent yield) of 99+ percent purity by liquid chromatography. The solid has the following H nuclear magnetic resonance spectrum: (DMSO d$_6$), delta: 2.20 (s, 12H), 2.30 (s, 6H), 4.10 (s, 4H), 5.40 (s, 1H), 6.90 (s, 1H), and it melts at from 295° C. to 297° C. The solid is identified as

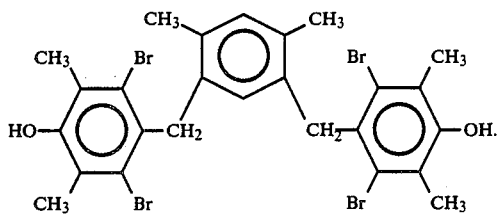

EXAMPLE 12

Alkylation of Polystyrene

A one-liter resin kettle, fitted with a reflux condenser and overhead stirrer, is charged with 50.0 g of general purpose heat-resistant polystyrene resin (STYRON ®685D, The Dow Chemical Company), 300 ml of methylene chloride and 0.030 g of anhydrous FeCl₃. The resulting solution is stirred continuously at room temperature while 22.0 g of tribromomesitol which is dissolved in 300 ml of methylene chloride is added over a 4-hour period. The reaction mixture is left to stir overnight at room temperature under a nitrogen atmosphere. The thus alkylated polystyrene is next recovered by precipitation into methanol and is washed three times with methanol. The product is next dried at 60° C. in vacuo overnight which yields 66.7 percent thus alkylated polystyrene. Instrumental neutron activation analysis of the thus alkylated polystyrene shows the polymer contains 12 (±0.3) weight percent bromine.

EXAMPLE 13

Modification of Styrene-Divinylbenzene Copolymer Beads

A creased 500-ml three-neck round-bottom flask, which is fitted with a reflux condenser, is charged with 20.8 g of macroporous 6/42 styrene-divinylbenzene copolymer beads, 20 mg of anhydrous FeCl₃ solid, and 250 ml of 1,2-dichloroethane. The mixture is stirred continuously and is heated to reflux temperature. Upon establishment of reflux, 37.3 g of solid tribromomesitol is added over a 30-minute period via a solid addition funnel. Upon completing the addition of the tribromomesitol, the mixture is stirred and is maintained at reflux for 4 hours. Next, the heating is terminated, and the mixture is allowed to cool to about 40° C. The thus modified copolymer beads are next collected on a medium porosity fritted glass funnel with vacuum filtration. The thus isolated beads are next transferred to a 500-ml Erlenmeyer flask and are washed by stirring as a slurry in 250 ml of 2-propanol at 50° C. for 15 minutes. Next, the wash liquor is removed by vacuum filtration through a fritted funnel. The copolymer beads are returned to the Erlenmeyer flask and are washed in the same fashion two additional times. Upon completion of the third washing, the thus isolated beads are rinsed with an additonal 250 ml of 2-propanol at 25° C. while on the glass frit. Upon drying in vacuo at 40° C. for 16 hours, 39.9 g of modified copolymer beads are obtained. The thus modified copolymer beads thus gain weight to indicate that 36 percent of the benzene rings in the copolymer contain the 2,6--dibromo-4-hydroxy-3,5-dimethylbenzyl moiety.

EXAMPLE 14

Alkylation of Bisphenol A Polycarbonate

A 6.35-g portion of bisphenol A polycarbonate, having an inherent viscosity of 0.525 deciliters/gram in methylene chloride at 25° C. at an approximate concentration of 0.5 g/deciliter, is dissolved in 35 ml of 1,2-dichloroethane. The solution is heated to reflux, and 2.0 mg of anhydrous FeCl₃ is added. Next, 2.35 g of tribromomesitol is added via a solid addition funnel. The mixture is maintained at reflux for 90 minutes, during which time HBr evolution is observed. Upon the completion of the 90 minutes, the heating is terminated, and the hot polymer solution is poured into 500 ml of well stirred methanol. The resulting polymer precipitate next is washed with methanol, is chopped three times in methanol in a blender and is dried in vacuo at room temperature overnight. Instrumental neutron activation analysis shows the alkylated polycarbonate contains 4.9 (±0.2) percent bromine.

EXAMPLE 15

Monoalkylation of 2,6-Dimethylphenol with 3,5-Dibromo-4-methoxymethyl-2,6-dimethylphenol A 6.48-g (0.02-mole) portion of 3,5-dibromo-4-methoxymethyl-2,6-dimethylphenol and 2.44 g (0.02 mole) of 2,6-dimethylphenol are suspended in 100 ml of carbon tetrachloride, and 0.2 g (0.001 mole) of p-toluene sulfonic acid is added. The mixture is heated to reflux and held there for 8.0 hours. Methanol is produced as a by-product. Cooling of the mixture and filtering of the insoluble solid affords 6.3 g of the thus monoalkylated product identical with the product of in Example 1. The product has 99+ percent purity by gas chromatography.

EXAMPLES 16-23

Alkylations with 3,5-dibromo-4-hydroxymethyl-2,6-dimethylphenol:

EXAMPLES 16-17

With added catalyst:

EXAMPLE 16

Monoalkylation of 2,6-Dimethylphenol

A 3.1-g (0.01-mole) portion of 3,5-dibromo-4-hydroxymethyl-2,6-dimethylphenol is suspended in 100 ml of toluene, and 1.22 g (0.01 mole) of 2,6-dimethylphenol is added, followed by 4.0 g of acidic DOWEX ® ion-exchange resin beads. The mixture is heated to reflux, and the distillate boiling below 110° C., containing some water, is removed. During the distillation, 100 ml of toluene is added to keep the amount of solvent constant. Upon removal of water, the mixture is kept at 110° C. for 1 hour, and the solution is filtered to separate the beads. Cooling of the solution to 25° C. affords a precipitate which is analyzed as 93 percent purity by gas chromatography. The solid is slurried in 20 ml of CH₂Cl₂ and is filtered to afford 1.4 g (34 percent yield) of 3,5-dibromo-2,2',6,6'-tetramethylbisphenol F, which is identified by nuclear magnetic resonance spectroscopy as being identical with the product of Example 1. It melts at 206° C.-208° C.

EXAMPLE 17

Monoalkylation of 2,6-Dimethylphenol

A 6.2-g (0.02-mole) portion of 3,5-dibromo-4-hydroxymethyl-2,6-dimethylphenol is slurried in 100 ml of carbon tetrachloride, and 2.4 g (0.02 mole) of 2,6-dimethylphenol is added, followed by 0.19 g (0.001 mole) of p-toluene sulfonic acid. The mixture is heated to reflux, 75° C., and is held there for 0.5 hour. Upon completion of this heating interval, the reaction is complete as determined by nuclear magnetic resonance spectroscopy. Cooling to 25° C. and filtration of the solid affords 6.0 g (73 percent yield) of dibromotetramethylbisphenol F as a white solid, identical with the product of Example 1.

EXAMPLES 18–23

Without added catalyst:

EXAMPLE 18

Monoalkylation of 2,6-Dimethylphenol

In a 100-ml round-bottom flask, 6.2 g (0.020 ml) of 3,5-dibromo-4-hydroxymethyl-2,6-dimethylphenol and 2.6 g of 2,6-dimethylphenol are suspended in 25 ml of nitrobenzene. The mixture is stirred continuously and is heated over a 30-minute period to 175° C. The stirring of the mixture is maintained, and the temperature is maintained at 175° C. for 1 hour. Next, the stirring mixture is cooled to room temperature. The resulting precipitate is collected by filtration and is dried overnight in vacuo. Liquid chromatographic analysis and $^1$H nuclear magnetic resonance and $^{13}$C nuclear magnetic resonance spectroscopic analyses show the resulting product to be identical with the product of Example 1.

EXAMPLE 19

Alkylation of Cresol Formaldehyde Novolac

To a one-liter reaction vessel equipped with temperature control and indicating means and a Dean-Stark trap with a reflux condenser, are added 227.5 g (1.96 eq.) of cresol formaldehyde novolac (softening point 78° C.), 80 g (0.258 eq.) of 3,5-dibromo-4-hydroxymethyl-2,6-dimethylphenol and 100 g of toluene. Upon stirring at room temperature and atmospheric pressure to thoroughly mix the contents, the temperature is raised to 115° C. During the course of reaction, the water by-product of the reaction is removed by azeotrope with toluene. The distillate is condensed, thereby forming two distinct phases, an aqueous (bottom) phase and a toluene (top) phase. The aqueous phase is cumulated inside the Dean-Stark trap, and the toluene phase overflow from the Dean-Stark trap is recycled back into the reactor. Completion of reaction is checked by liquid chromatography for the disappearance of the reactant, 3,5-dibromo-4-hydroxymethyl-2,6-dimethylphenol, in the reaction mixture. The reaction is complete in 2 hours as is indicated by the complete disappearance of said reactant in the liquid chromatograph and by the cumulation of the theoretical amount of water in the Dean-Stark trap.

The resulting solution is next distilled under vacuum at a temperature of 160° C. to generally remove all toluene. The resulting novolac contains 13.1 percent bromine and has a softening point of 99° C.

EXAMPLE 20

Alkylation of Phenol Formaldehyde Novolac

Phenol formaldehyde novolac (150 g, 1.47 eq., softening point 60° C.), 52.5 g (0.169 eq.) of 3,5-dibromo-4-hydroxymethyl-2,6-dimethylphenol and 100 g of toluene are combined in the same manner as Example 19. Upon removal of toluene, the resulting novolac contains 13.2 percent bromine and has a softening point of 83.7° C.

EXAMPLE 21

Alkylation of Dicyclopentadiene Phenol Novolac

Dicyclopentadiene phenol novolac (200 g, 1.21 eq., softening point 90° C.), 70 g (0.226 eq.) of 3,5-dibromo-4-hydroxymethyl-2,6-dimethylphenol and 150 g of toluene are combined in the same manner as Example 19. Upon removal of solvent, the resulting novolac contains 13.43 percent bromine and has a softening point of 108.7° C.

EXAMPLE 22

Alkylation of 1,1,1-Tri(hydroxyphenyl)methane 1,1,1-Tri(hydroxyphenyl)methane (196 g, 2.0 eq., softening point 112° C.), 70 g (0.226 eq.) of 3,5-dibromo-4-hydroxymethyl-2,6-dimethylphenol and 150 g of methyl isobutyl ketone are combined in the same manner as Example 19. Upon removal of methyl isobutyl ketone, the resulting novolac contains 15.23 percent bromine and has a softening point of 134° C.

EXAMPLE 23

Alkylation of Polystyrene

A. Neat Preparation

A Brabender mixer (Model R.0.6.), which is heated to 200° C. and is operating at 63 rpm, is charged with 37.4 g of general purpose heat-resistant polystyrene (STRON ®685D, The Dow Chemical Company). Upon the completion of about 3 minutes, a homogeneous melt phase is obtained, and 13.8 g of 3,5-dibromo-4-hydroxymethyl-2,6-dimethylphenol is added over a 5-minute period. Mixing is continued an additional 25 minutes, during which time steam evolution is evident. The resulting polymer is next recovered and is cooled to room temperature on a stainless steel table. The polymer subsequently is dissolved in methylene chloride, is filtered, is recovered by precipitation into methanol and is washed three times in methanol. The product is dried overnight at 60° C. in vacuo. Instrumental neutron activation analysis shows the resulting alkylated polystyrene to contain 8.4 (±0.4) percent bromine.

B. Testing for Improved Ignition Resistance

A sample of the alkylated polystyrene of Part A is blended with $Sb_2O_3$ (3.5 weight percent of total). Vertical burning tests (UL Standard 94) are conducted with compression molded samples of the $Sb_2O_3$-doped polymer. The polymer exhibits combustion behavior consistent with a UL 94 V-O classification. This shows improved flame-retardant efficiency is obtained.

EXAMPLES 24–27

Expoxidation of alkylated novolac resins:

EXAMPLE 24

Epoxidation of
2,6-Dibromo-4-hydroxy-3,5-dimethylbenzyl containing Cresol Formaldehyde Novolac To a 2-liter reaction vessel which is equipped with temperature and pressure control and indicating means, a means for the continuous addition of aqueous sodium hydroxide, a means for condensing and separating water from a codistillate mixture of water, solvent and epichlorohydrin and means for returning the solvent and epichlorohydrin to the reaction vessel, is added 393.1 g (2.7995 eq.) of 2,6-dibromo-4-hydroxy-3,5-dimethylbenzyl containing cresol formaldehyde novolac as from Example 19, 1554 g (16.8 eq.) of epichlorohydrin and 1035 g of the methyl ether of propylene glycol (1-methoxy-2-hydroxypropane) as a solvent. Upon stirring at room temperature and atmospheric pressure to thoroughly mix the contents, the temperature is raised to 55° C. and the pressure is reduced to 105 mm Hg absolute. To the resulting solution is continuously added 220.6 g (2.7575 eq.) of 50 percent aqueous sodium hydroxide solution at a constant rate over a period of 3 hours.

During the addition of the sodium hydroxide, the water is removed by codistilling with epichlorohydrin and solvent. The distillate is condensed, thereby forming two distinct phases, an aqueous phase (top) and an organic epichlorohydrin solvent phase (bottom). The organic phase is continuously returned to the reactor. Upon completion of the sodium hydroxide addition, the reaction mixture is maintained at a temperature of 55° C. and a pressure of 105 mm Hg absolute for an additional 30 minutes. The resulting glycidyl ether next is distilled under full vacuum and at a temperature of up to 160° C. to generally remove all epichlorohydrin and 1-methoxy-2-hydroxypropane. The molten glycidyl ether product is diluted to 20 percent resin concentration with a 75/25 methyl ethyl ketone/toluene solvent mixture, and the diluted product is next washed with deionized water several times to remove NaCl. The organic phase from the water washes is placed on a rotary evaporator under a vacuum and at a temperature of 160° C. to remove the solvent. The resulting polyglycidyl ether has an epoxide content of 19.4 percent and contains 9.53 percent bromine, and has a softening point of 75.6° C. This is the most preferred epoxy for use in an electronic encapsulation formulation.

EXAMPLE 25

Epoxidation of
2,6-Dibromo-4-hydroxy-3,5-dimethylbenzyl containing Phenol Formaldehyde Novolac The general procedure of Example 24 is used to prepare this epoxy resin. The phenol formaldehyde novolac is as from Example 20. The resulting epoxy resin has an epoxide content of 21.5 percent, containing 8.62 percent bromine, and has a softening point of 62° C.

EXAMPLE 26

Epoxidation of
2,6-Dibromo-4-hydroxy-3,5-dimethylbenzyl containing Dicyclopentadiene Phenol Novolac The general procedure of Example 24 is used to prepare this epoxy resin. The dicyclopentadiene phenol novolac is as from Example 21. The resulting epoxy resin has a softening point of 74.9° C. containing 16.27 percent epoxide and 9.91 percent bromine.

EXAMPLE 27

Epoxidation of
2,6-Dibromo-4-hydroxy-3,5-dimethylbenzyl-containing 1,1,1-Tri(hydroxyphenyl)methane The general procedure of Example 24 is used to prepare this epoxy resin. The 2,6-dibromo-4-hydroxy-3,5-dimethylbenzyl-containing 1,1,1-tri(hydroxyphenyl)methane is as from Example 22. The resulting epoxy resin has a softening point of 89.7° C., containing 20.87 percent epoxide and 9.6 percent bromine.

EXAMPLE 28

Use in Encapsulation with Comparative Formulation

I. Total Hydrolyzable Halide

The sample to be analyzed is saponified by KOH reflux, and the resulting halides which are extracted are titrated argentometrically by a potentiometric technique, as follows: weigh into a 250 Erlenmeyer flask 2 g of sample, add 30 ml of 1,4-dioxane and stir until the sample dissolves. Preset a heat source which permits the sample to begin reflux in 4-6 minutes (240-360 seconds). Add 30 ml of 3N ethanolic KOH solution, and next attach a condenser to the flask, and heat to reflux with constant stirring. Reflux 30 minutes (1800 seconds), with the initial time (0 second) as the moment the first condensed drop of liquid falls back into the flask from the condenser. Add 20 ml of 20 percent nitric acid to the flask. Add 50 ml of deionized water; next cool the solution to room temperature. Calibrate an ion meter with a Ag/AgCl and $KNO_3$-type electrodes to read 0 mV against a NaCl reference solution. Titrate the sample mixture with standard silver nitrate solution (0.025N aqueous), insuring that the sample mixture is spinning and the electrodes are free of resin. From the volume of titrant used, calculate the hydrolyzable chloride and hydrolyzable bromide.

II. Formulation

Each of the products of Examples 24 and 26 and a control resin are formulated into an electrical encapsulating formulation. The formulations are each cured at 175° C. for 4 hours (14400 seconds). The encapsulating formulations are given in Table I.

The properties of the cured encapsulating formulations are determined by the following procedures, except the total hydrolyzable halides which are determined on the epoxy resins themselves. The results are given in Tables II, III and IV, etc.

III. Moisture Absorption

The moisture pick-up is determined by placing preweighed 1/16" thick ×4" diameter cured disks in an autoclave at 15 psig (gauge pressure of 103 kPa) steam, 121° C., for 500 hours ($1.8 \times 10^6$ seconds). The disks are removed and are cooled at ambient temperature (25° C.) for about 15-30 minutes (900-1800 seconds), and next the disks are wiped dry and are again weighed to determine any weight difference. The results are given in Table III.

IV. Dielectric Constant

The dielectric constant is determined by the use of a Gen Rad 1689 bridge and LD-3 cell. Coupons approximately 3"×3"×1/16" (76.2 mm×76.2 mm×1.600 mm) are cut from each cured formulated disk and are measured with the Gen Rad 1689 bridge and LD-3 cell at the ambient temperature. The frequencies used are $1 \times 10^3$ Hz, $10 \times 10^3$ Hz, and $100 \times 10^3$ Hz.

V. Device Reliability Testing

The device testing is determined by a highly accelerated stress test, which involves the following conditions: 121° C., 15 psig steam, and 25 volts bias. The device is a 14-pin LM 324 quad operational amplifier with a single passivation layer. The percentage of devices that fail as a function of time are given in Table IV.

TABLE I

| | Encapsulation Formulation | | |
|---|---|---|---|
| Component | Co.* | A | B |
| Epoxy Resin I Type/g | 174.7 | about 59.3 | about 0.0 |
| Epoxy Resin II Type/g | Control/ 26.3 | Ex. 24/about 136.7 | Ex. 26/about 201.0 |
| Curing Agent, g | 89.75 | about 94.75 | about 72.50 |
| triphenyl-phosphine, g | 2.25 | 2.25 | 2.50 |
| Mold release agent, g | 4.0 | 4.0 | 6.0 |
| Epoxy silane, g | 4.0 | 4.0 | 4.0 |
| Fused silica, g | 685.0 | 685.0 | 700.0 |
| Antimony Oxide (Sb$_2$O$_3$), g | 10.0 | 10.0 | 10.0 |
| Carbon Black, g | 4.0 | 4.0 | 4.0 |
| % Bromine in Formulation | 1.25 | 1.25 | 2.00 |

*Comparative
Epoxy Resin I is Quatrex ® 3410, a cresol epoxy novolac having an epoxide equivalent weight (equiv. wt.) of about 216 and a viscosity of about 372 centistokes at 150° C.
Epoxy Resin II is as listed, with the control Quatrex ® 6410, a solid generally ortho-brominated epoxy resin.
The curing agent is a phenol-formaldehyde novolac resin with an average hydroxyl functionality of 6 and a phenolic hydroxyl equiv. wt. of about 104. (Schenectady Chemical, HRJ-2210).
The mold release agents are refined Montan waxes (OP; E) as available from Hoechst.
The epoxy silane is Z-6040 available from Dow Corning Corp.

TABLE II

| | Total Hydrolyzable Halide Analysis | |
|---|---|---|
| Sample Number | Hydrolyzable Chloride, ppm | Hydrolyzable Bromide, ppm |
| Co.* | 240 | 180 |
| A | 209 | 0 |
| B | 254 | 0 |

*Comparative

TABLE III

| | Moisture Absorption |
|---|---|
| Sample Number | % Weight Gain |
| Co* | 0.93 |
| A | 0.83 |
| B | 0.75 |

*Comparative

Dielectric constant in each of the Comparative, the A, and the B formulations is generally equivalent.

TABLE IV

| | Device Reliability | | |
|---|---|---|---|
| Sample Number | % Device Failure | | |
| | 400 hrs | 600 hrs | 800 hrs |
| Co* | 25 | 75 | 100 |
| A | 3 | 7 | 28 |
| B | 0 | 2 | 15 |

*Comparative

Thus, it can be seen that these stable meta-bromine-containing formulations give substantially better performances than the conventional systems.

We claim:

1. A coupled aromatic compound represented by the formula

Ar-Y wherein Ar is an aromatic moiety different from Y and Y is an aromatic moiety represented by one of the formulae:

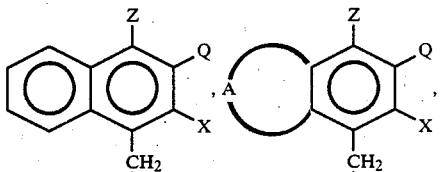

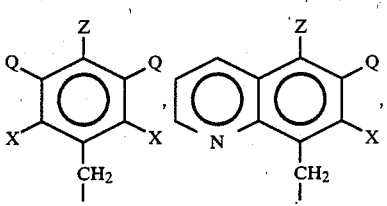

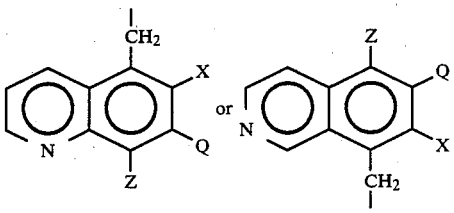

wherein
A is an aliphatic ring system bonded to the aromatic ring;
Q is separately at each occurrence hydrogen, alkyl or inertly-substituted alkyl provided that the carbon bonded to the aromatic ring is a primary or secondary carbon;
X is separately at each occurrence a halogen moiety; and
Z is a nitrogen- or chalcogen-containing moiety.

2. The compound of claim 1 wherein X is Br or Cl and Z is NH$_2$, NHR, NR$_2$, OH, OR,

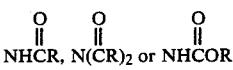

wherein R is hydrocarbyl having from 1 to 12 carbons.

3. The compound of claim 2 wherein Q is alkyl having 1 to 12 carbons, Z is OH and X is Br.

4. The composition of claim 1 which is a novolac resin containing at least ½ percent by weight of the moiety represented by Y.

5. The composition of claim 4 wherein the Y moiety is a 2,6-dihalo-4-hydroxy-3,5-di($C_{1-10}$ alkyl)benzyl moiety.

6. The composition of claim 5 wherein the 2,6-dihalo-4-hydroxy-3,5-di($C_{1-10}$ alkyl)benzyl moiety is 2,6-dibromo-4-hydroxy-3,5-dimethylbenzyl.

7. The composition of claim 6 wherein the weight percent of bromine attributable to 2,6-dibromo-4-hydroxy-3,5-dimethylbenzyl moieties is from about one to 20 percent.

8. The composition of claim 7 wherein the weight percent of bromine is from about 5 to about 15 percent.

9. The composition of claim 1 which is a cured epoxy thermoset containing at least ½ percent by weight of the moiety represented by Y.

10. The composition of claim 9 which contains from about ½ to about 20 percent by weight of halogen attributable to Y moieties.

11. The composition of claim 10 wherein the Y moieties are 2,6-dihalo-4-hydroxy-3,5-di($C_{1-10}$ alkyl)benzyl moieties.

12. The composition of claim 9 which is an encapsulation formulation suitable for electronic use.

13. The composition of claim 12 wherein the Y moieties contain 2,6-dibromo-4-substituted oxy-3,5-dimethylbenzyl moieties with the 2,6-dibromo moieties present from about ½ to about 3 weight percent of the encapsulation formulation which has as the cured epoxy thermoset resin a cured epoxy thermoset prepared from at least, an epoxidized cresol formaldehyde novolac or an epoxidized dicyclopentadiene phenol novolac, each containing said Y moieties.

14. The composition of claim 1 which is an aromatic-containing polymeric resin which contains at least ½ percent by weight of the moiety represented by Y.

15. A process for the preparation of the coupled aromatic compound of claim 1 which process comprises contacting an aromatic compound with an alkylating aromatic agent represented by the formula (hm)-Y wherein hm is Br, Cl, OH or $C_{1-4}$ alkoxy and Y is represented by the formulae:

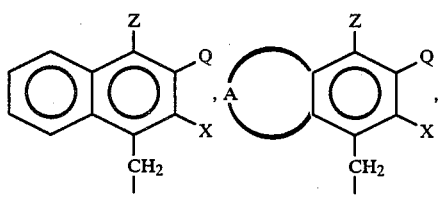
,

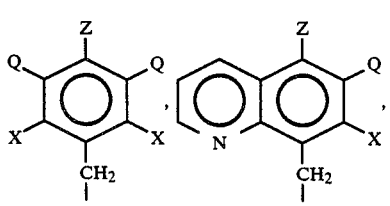
,

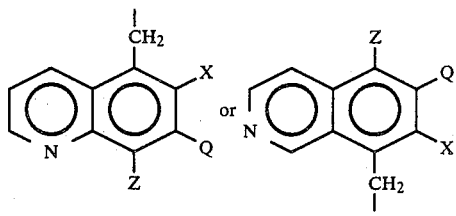

under conditions sufficient to form the coupled aromatic compound.

16. The process of claim 15 wherein the alkylating agent is represented by the formula:

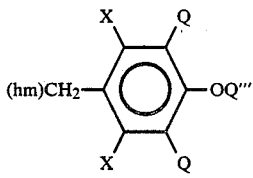

wherein
X is separately at each occurrence a halogen moiety selected from the group consisting of fluoro, chloro and bromo;
Q is separately at each occurrence hydrogen, or $C_{1-12}$ alkyl or inertly-substituted alkyl, each with at most a secondary carbon attached to the six-membered ring; and
Q''' is H or organic.

17. The process of claim 16 wherein
X is separately at each occurrence a halogen moiety selected from the group consisting of chloro and bromo;
Q is methyl; and
Q''' is H.

18. The process of claim 17 wherein the agent is 4-bromomethyl-3,5-dibromo-2,6-dimethylphenol.

19. The process of claim 17 wherein the agent is 3,5-dibromo-4-hydroxymethyl-2,6-dimethylphenol.

20. The process of claim 16 wherein the aromatic compound is selected from the group consisting of alkyl phenols and novolacs.

21. The process of claim 19 wherein the aromatic compound is a hydroxy-containing aromatic.

22. The process of claim 21 wherein the hydroxy-containing aromatic is a novolac resin.

23. The process of claim 18 wherein the aromatic compound is alkyl phenol.

24. The process of claim 16 wherein the aromatic compound is a hydroxy-containing aromatic and further wherein etherification with an epichlorohydrin is carried out to prepare a vicinal halohydrin organo-oxy containing meta-halo-phenoxy-coupled aromatic.

25. The process of claim 24 further wherein epoxidation of the vicinal halohydrin organo-oxy moiety is carried out to prepare a meta-halo-phenoxyepoxy-coupled aromatic.

26. The process of claim 25 wherein the epihalohydrin is epichlorohydrin, and the meta-halo-phenoxyepoxy-coupled aromatic contains a 2,3-epoxypropoxy moiety.

27. The process of claim 25 further wherein the meta-halo-phenoxyepoxy-coupled aromatic is cured to prepare a cured epoxy system.

28. The process of claim 27 wherein the cured epoxy system contains 4-oxy-3,5-dimethyl-2,6-dibromobenzyl which is coupled at the 4-oxy and benzylic positions.

29. The process of claim 27 wherein a meta-halo-phenoxy-coupled aromatic is used as the curing agent to prepare a cured epoxy system containing a coupled oxyhalomesitylic moiety.

* * * * *